| United States Patent [19]
Perrin

[11] 3,954,892
[45] May 4, 1976

[54] PROCESS FOR THE PURIFICATION OF PARA-NITROPHENOL

[75] Inventor: André Perrin, Isere, France

[73] Assignee: Rhone-Poulenc, S.A., Paris, France

[22] Filed: Mar. 13, 1973

[21] Appl. No.: 340,903

[30] Foreign Application Priority Data
Mar. 14, 1972  France .............................. 72.008814

[52] U.S. Cl................................................ 260/622 R
[51] Int. Cl.² .................................................. C07C 79/26
[58] Field of Search ..................... 260/622 R, 621 R

[56] References Cited
UNITED STATES PATENTS 2,802,883  8/1957  Dietzler........................... 260/622 R
2,811,565  10/1957  Alexander et al............... 260/622 R
2,868,844  1/1959  Coffield et al.................... 260/622

*Primary Examiner*—James O. Thomas, Jr.
*Assistant Examiner*—W. B. Lone
*Attorney, Agent, or Firm*—Stevens, Davis, Miller & Mosher

[57] ABSTRACT

In the nitration of phenol with nitric acid, decantation of the residual acid, and steam distillation of ortho-nitrophenol to leave an aqueous distillation residue of para-nitrophenol, a cleaner purer crystalline para-nitrophenol product is obtained by cooling the hot distillation residue when it contains at least 0.5% of sodium bisulphite and is at pH 5.4 to 6.4.

8 Claims, No Drawings

PROCESS FOR THE PURIFICATION OF PARA-NITROPHENOL

This invention relates to a process for the purification of para-nitrophenol obtained by nitration of phenol.

Nitration of phenol by means of dilute or concentrated nitric acid is generally carried out in a solvent medium (e.g. an aromatic hydrocarbon) and leads essentially to a mixture of ortho-nitrophenol and para-nitrophenol in variable proportions depending on the process used. After nitration, the residual nitric acid is decanted, the solvent is removed and, preferably after having neutralised the organic layer containing the nitrophenols, the ortho-nitrophenol is separated from the para-nitrophenol by steam distillation of the ortho-isomer. Para-nitrophenol is thus obtained in the form of a crude aqueous distillation residue. It is then necessary to purify the nitrophenols. Hitherto, it has not been possible to carry out this purification by a simple process and it has been necessary in practice to convert the nitrophenols to their sodium derivatives, to isolate the latter and to convert them once again to the nitrophenols [GATTERMAN : Manuel pratique de chimie organique (Practical Manual of Organic Chemistry), p. 2478 (1946)]. Such a purification treatment involves considerable consumption of sodium hydroxide and acid, generally sulphuric acid, and is thus not economic, especially as according to GATTERMAN, it can be necessary to repeat this treatment until nitrophenol of sufficient purity is obtained.

The present invention provides a process for the preparation of para-nitrophenol which comprises nitration of phenol with nitric acid, isolation of the crude mixture of nitrophenols by decanting the residual aqueous solution of nitric acid, and steam distillation of ortho-nitrophenol to obtain a crude aqueous distillation residue of para-nitrophenol, crystallizing the para-nitrophenol by cooling the crude aqueous distillation residue containing dissolved para-nitrophenol when the distillation residue contains sodium bisulphite in a concentration of at least 0.5% and is at a pH of 5.4 to 6.4 and finally separating crystals of para-nitrophenol. (In this specification percentages are by weight).

Preferably the crude aqueous distillation residue containing dissolved para-nitrophenol from the steam distillation is treated so that the distillation residue contains sodium bisulphite in a concentration of at least 0.5% and the pH of the distillation residue is adjusted (if necessary) to 5.4 to 6.4, the treatment and pH adjustment being carried out in either order.

The bisulphite (or compounds capable of forming the bisulphite in situ can be added to the crude mixture of o- and p-nitrophenols during or after neutralizing the mixture obtained by decantation from the residual nitric acid, or preferably to the crude aqueous distillation residue containing p-nitrophenol, the o-isomer having been previously removed by steam distillation. The remainder of the description, for simplicity, refers to the preferred process.

At the end of the process it is sufficient to crystallise the para-nitrophenol and to collect it after filtration and washing with water. This process is very particularly valuable since it avoids the intermediate route via the sodium derivative.

The nitration with dilute or concentrated (e.g. 58%) nitric acid is usually carried out in a solvent medium such as an aromatic hydrocarbon e.g. benzene. The solvent e.g. benzene is removed by distillation before the end of the steam distillation.

The adjustment of the pH and the introduction of the necessary amount of sodium bisulphite, which can be carried out in either order, are carried out at a temperature which is sufficiently high to ensure that the para-nitrophenol is completely dissolved in the medium.

The treatment is usually carried out on an aqueous distillation residue in which the concentration of para-nitrophenol is between 10 and 50%, and preferably between 15 and 30%.

The pH of the aqueous distillation residue can be adjusted by addition of acid or alkali. According to a preferred procedure, the slightly acid organic solution containing the nitrophenol isomers is neutralised by means of an aqueous solution of sodium sulphite the solvent followed by the o-nitrophenol are then removed to leave a slightly alkaline aqueous distillation residue of p-nitrophenol, to which a suitable amount of acid is added to adjust the pH. The acid may be a strong inorganic acid such as sulphuric acid or phosphoric acid or an organic acid such as acetic acid. The pH is preferably adjusted to 5.8 to 6.1 but in practice, it is very particularly recommended to adjust the pH of the aqueous solution of para-nitrophenol to pH 6.

The aqueous solution of para-nitrophenol is treated with sodium bisulphite, or with any body which is capable of generating the latter, in such a way that the solution has a concentration of sodium bisulphite of at least 0.5%. This concentration is usually 0.5 to 5% and is preferably 1.5 to 3%. Of course, it is possible to use bisulphite concentrations much greater than the upper limits mentioned above, without disadvantage to the process, but in practice, however, there is no value in exceeding these limits.

If the acid organic layer containing the mixture of nitrophenols has been neutralised by adding a solution of sodium sulphite as stated above, the aqueous distillation residue of para-nitrophenol obtained subsequently already contains a little bisulphite. It is then sufficient to add a suitable amount of sodium bisulphite so that the concentration is within the limits defined above.

The crystals of para-nitrophenol obtained after cooling the treated distillation residue have properties which are identical to those of the crystals obtained by the purification treatments of the prior art based on the conversion to the sodium derivative. Para-nitrophenol purified according to the process of the invention has in particular only a slight colouration which does not intensify on ageing, and it is substantially free from tars, polynitrophenols and quinone impurities. It can be used directly for producing pharmaceutical compounds of Codex quality, such as para-acetylamino-phenol.

The example which follows illustrates the invention:

EXAMPLE

Phenol dissolved in benzene is nitrated continuously by means of 58% nitric acid and the organic layer containing the mixture of ortho- and para-nitrophenol is separated from the residual nitric acid by decantation. The acid organic layer is successively neutralised by means of an aqueous solution of sodium sulphite, distilled until the benzene is removed and treated with steam in order to remove ortho-nitrophenol by steam distillation. An aqueous distillation residue of para-nitrophenol is thus obtained, the composition of which is substantially as follows:

| para-nitrophenol (contaminated with tars, dinitrophenols and quinone derivatives; estimation of the impurity content: 3%) | 18 % |
| --- | --- |
| sodium salt of para-nitrophenol | 0.95 % |
| sodium bisulphite | 0.55 % |
| water | 80.5 % |

2,100 g of the aqueous distillation residue of para-nitrophenol are removed and kept at 70°C; 40 g of a solution of sodium bisulphite containing 12 g of bisulphite are added to it and then 10 g of 50% sulphuric acid are introduced at this temperature so as to adjust the pH to 6. After stirring and cooling to 20°C, the mixture is filtered to separate paranitrophenol, which is washed with 400 ml of water. Para-nitrophenol obtained has the following characteristics

| Melting point | 113° | |
| --- | --- | --- |
| Hydroquinone | content less than | 0.0250% |
| Phenol | " | 0.0250% |
| 2,6-Dinitrophenol | " | 0.0100% |
| 2,4-Dinitrophenol | " | 0.0100% |
| ortho-Nitrophenol | " | 0.0250% |

(the upper limits for the impurity contents are determined by thin layer chromatography).

I claim:

1. In a process for the separation and purification of para-nitrophenol from the reaction product of the nitration of phenol with nitric acid, isolation of the crude mixture of nitrophenols by decanting the residual aqueous solution of nitric acid and steam distillation of ortho-nitrophenol to obtain a crude aqueous distillation residue containing dissolved para-nitrophenol, from which crystals of para-nitrophenol are precipitated on cooling and physically separated therefrom, the improvement which consists in treating the crude distillation residue containing dissolved para-nitrophenol so that it contains sodium bisulphite in a concentration of at least 0.5%, and if the pH of the distillation residue is not from 5.4 to 6.4 adjusting the pH of the distillation residue to 5.4 to 6.4 to precipitate crystals of para-nitrophenol.

2. A process according to claim 1 wherein the pH is adjusted to 5.8 to 6.1.

3. A process according to claim 1 wherein the concentration of sodium bisulphite is 0.5 to 5%.

4. A process according to claim 1 wherein the concentration of para-nitrophenol in the crude aqueous distillation residue is 15 to 30%.

5. A process according to claim 1 wherein sodium bisulphite is added to the crude aqueous distillation residue.

6. The process according to claim 1 wherein sodium bisulphite is added and then, if necessary, the pH is adjusted to 5.4 to 6.4.

7. The process according to claim 1 wherein the pH is adjusted to 5.4 to 6.4 and then sodium bisulphite is added.

8. In a process for the separation and purification of para-nitrophenol from the reaction product of the nitration of phenol with 58% nitric acid in benzene, isolation of the crude mixture of nitrophenols by decanting the residual aqueous solution of nitric acid and steam distillation of ortho-nitrophenol to obtain a crude aqueous distillation residue containing dissolved para-nitrophenol, from which crystals of para-nitrophenol are precipitated on cooling, the improvement which consists in neutralising the decanted organic layer with sodium bisulphite, distilling it to remove benzene, treating the crude aqueous distillation residue, obtained on steam distillation, at 70°C. with sodium bisulphite so that it contains at least 0.5% sodium bisulphite, adding sulphuric acid to adjust the pH to 6 and then cooling to deposit crystals of para-nitrophenol and physically separating said para-nitrophenol.

* * * * *